United States Patent [19]

Winston et al.

[11] Patent Number: 4,851,354
[45] Date of Patent: Jul. 25, 1989

[54] APPARATUS FOR MECHANICALLY STIMULATING CELLS

[75] Inventors: Flaura K. Winston, Narberth; Lawrence E. Thibault, Paoli; Edward J. Macarak, Havertown, all of Pa.

[73] Assignee: Trustees of the University of Pennsylvania, Philadelphia, Pa.

[21] Appl. No.: 129,262

[22] Filed: Dec. 7, 1987

[51] Int. Cl.[4] .............................................. C12M 3/00
[52] U.S. Cl. .................................. 435/284; 435/285; 435/296
[58] Field of Search ............... 435/284, 285, 286, 296, 435/297, 298, 299; 215/6

[56] References Cited

U.S. PATENT DOCUMENTS 3,591,461  7/1971  Bazil et al. ........................... 435/298

OTHER PUBLICATIONS

Winston, F. K., et al., Abstract of a paper entitled "The In Vitro Response of Endothelium to Mechanical Loading," 38th ACEMB in Chicago, Ill. from 9/30–10/2/85.
Thibault, L. E. and Fry, L., "Mechanical Characterization of Membranelike Biological Tissue," *J. Biomech. Eng.* 105:31–38 (1983).
Davies, Peter F., et al., "Influence of Hemodynamic Forces on Vascular Endothelial Function," *J. Clin. Invest.*, 73:1121–1129 (4/1984).
Leung, Donald Y. M., et al., "Cyclic Stretching Stimulates Synthesis of Matrix Components by Arterial Smooth Muscle Cells In Vitro," *Science,* 191:475–577 (1976).
Gorfien, S. F., et al., Abstract of a paper entitled "Fibronectin and Type III Collagen Production by Bovine Pulmonary Artery Endothelium Subjected to Cyclic Biaxial Strain," Cell Bio Meeting in Washington, D.C. on 12/7/86.
Winston, F. K., et al., Paper entitled "Response of Endothelial Cells in Culture to Biaxial Deformation," Northeast Bioengineering Conference in Phila. on 3/87.
B. E. Sumpio, et al., "Mechanical Stress Stimulates Aortic Endothelial Cells to Proliferate," *Journal of Vascular Surgery,* 1987; 6:252–6.
B. E. Sumpio, et al., "Alterations in Aortic Endothelial Cell Morphology and Cytoskeletal Protein Synthesis During Cyclic Tensional Deformation," *Journal of Vascular Surgery,* 1988; 7:130–8.
A. J. Banes, et al., "A New Vacuum-Operated Stress-Providing Instrument that Applies Static or Variable Duration Cyclic Tension or Compression to Cells in Vitro," *J. Cell Sci.* 75, 35–42 (1985).
Sales Literature of Flexcell Corp., Apr. 1988.

*Primary Examiner*—Albert J. Makay
*Assistant Examiner*—Noah Kamen
*Attorney, Agent, or Firm*—Woodcock Washburn Kurtz Mackiewicz & Norris

[57] ABSTRACT

An apparatus useful for studying cells in culture under conditions which reproduce their natural, in vivo mechanical environment is disclosed. The device comprises an airtight well having an optically transparent compliant base of a biologically compatible material on which said cells may be grown and an optically transparent, removable cap, coupled with a ported, airtight reservoir which reservoir has an optically transparent base and which reservoir can be filled with pressurizing media to create cyclic variations in hydrostatic pressure beneath said compliant base, causing said compliant base to deform and thereby exert a substantially uniform biaxial strain on the cells attached thereto.

10 Claims, 1 Drawing Sheet

U.S. Patent  Jul. 25, 1989  4,851,354
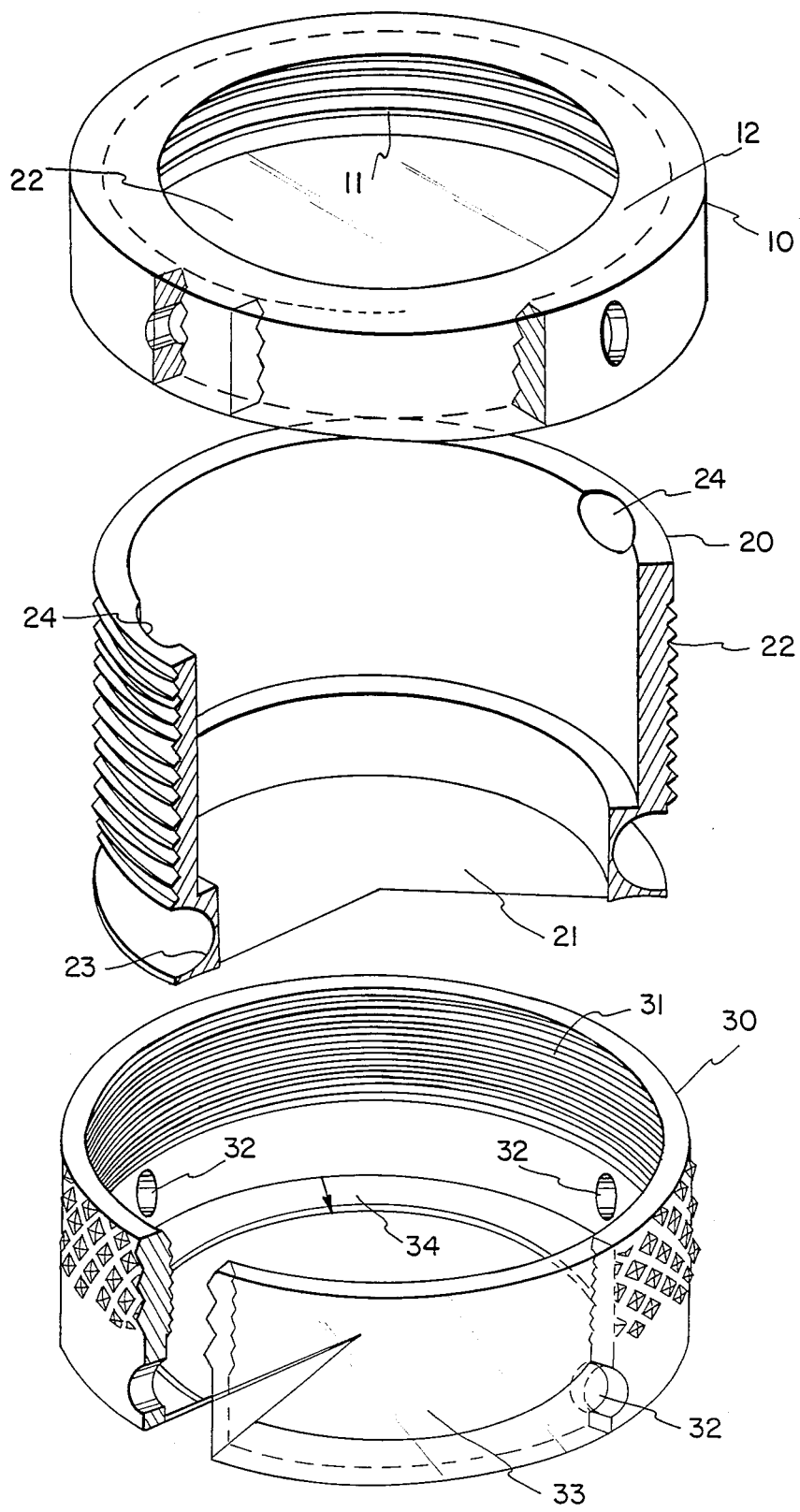

APPARATUS FOR MECHANICALLY STIMULATING CELLS

BACKGROUND OF THE INVENTION

This invention relates to an apparatus useful for studying cells in culture under conditions which reproduce their natural, in vivo mechanical environment. Use of the apparatus of this invention enables one to study the changes in the biochemistry and physiology of cultured cells under conditions of mechanical strain as compared to cells grown conventionally under quiescent conditions.

Mechanical stimulation of cells is believed to influence the biochemistry and physiology of cells, in particular, enhanced production and, therefore, improved harvesting efficiency of biochemical products from these cells. Various systems have been proposed previously for growing cells in culture. A few systems have attempted to account for the natural mechanical environment of cells. One typical prior art system (Leung, D., et al, *Science* 191:475–477, 1976), attempts to uniaxially elongate smooth muscle cells in culture, but fails in three general categories, namely, (1) uniaxial stretch is not physiologic, (2) the system does not allow for microscopic visualization of the cells, and (3) the strain distribution in this system is not uniform and, therefore, not well-characterized for the population of cells stimulated.

In another typical prior art system (Davies, P. et al, *J. Clin. Invest.* 73:1121–1129, 1984), cells in culture are subjected to a uniform shear strain, constant in magnitude and direction. This system fails in two general areas, namely, (1) endothelial cells are the only cells subjected to shear strain in vivo thereby limiting its applicability to only this one cell type and (2) shear strain in vivo occurs simultaneously with biaxial tension, and, by uncoupling the two, the true mechanical environment of endothelial cells is not reproduced.

SUMMARY OF THE INVENTION

A system has now been devised which more accurately reproduces the natural mechanical environment of cells by subjecting those cells to a uniform biaxial strain. The system of this invention comprises
  an airtight well having an optically transparent compliant base of a biologically compatible material on which said cells may be grown and an optically transparent, removable cap, and
  a ported, airtight reservoir coupled with said well beneath said compliant base, which reservoir has an optically transparent base and which reservoir can be filled with pressurizing medium to create cyclic variations in hydrostatic pressure beneath said compliant base, causing said compliant base to deform and thereby exert a substantially uniform biaxial strain on the cells attached thereto.

This invention further relates to a method for studying cells in culture under conditions which reproduce their natural, in vivo mechanical environment comprising seeding said cells on the compliant base of the above-mentioned device, allowing said cells to become confluent and attach to said compliant base, and subjecting said compliant base and the cells attached thereto to a cyclic biaxial strain by injecting and withdrawing pressurizing medium from said reservoir.

Accordingly, a main object of this invention is to provide an improved method of culturing cells under their natural, in vivo mechanical environment which overcomes the deficiencies and disadvantages of prior systems employed for this purpose.

A further object of this invention is to provide a chamber in which cultured cells can be subjected to a well-characterized state of biaxial strain, uniform over substantially the entire cell population, which reproduces their natural, in vivo mechanical environment.

A still further object of this invention is to provide a novel and improved system for increasing the yield and, therefore, the harvesting efficiency of biochemical products produced by cells in culture.

A still further object of this invention is to provide for direct microscopic visualization of the deforming cells, allowing for immersion or inverted microscopy under fluorescence, phase contrast, bright field or the like.

A still further object of this invention is to provide for adaptability of the system to any cell type.

A still further object of this invention is to provide for the maintenance and sampling of the cell culture so that conventional biochemical and physiologic assays can be performed with ease under sterile conditions.

A still further object of this invention is to provide for compatibility of the system with conventional cell culturing techniques.

A still further object of the invention is to provide for the system's use in either conventional incubators or in warm rooms or the like.

A still further object of this invention is to provide for gas or autoclave sterilization or the like of the assembled apparatus.

A still further object of this invention is to provide for the ability to vary the magnitude and temporal nature of the mechanical strain applied to the cells.

A still further object of this invention is to provide for reusability of the system.

Further objects and advantages of the invention will become apparent from the following description and claims.

BRIEF DESCRIPTION OF THE DRAWING

The figure is a sectional view of the device of this invention in unassembled form.

DETAILED DESCRIPTION OF THE INVENTION

The following description of a preferred embodiment of this invention refers to the figure. The device of this invention serves as a cell culture chamber and comprises a cap 10, a well 20 with a compliant base 21 on which the cells are grown, and a ported reservoir 30. The cap 10, well 20, and reservoir 30 are fabricated of a biologically compatible material such as, but not limited to, stainless steel and are preferably designed to fit on a microscope stage. A regulated positive displacement pump or pressure/vacuum source may be connected to the reservoir 30 for purposes of distending the compliant base 21. Conventional timing circuitry is provided to permit one to select the duty cycle of the mechanical stimulation. Conventional control features are provided so that the magnitude of the strain and the strain rate can be set.

In the illustrated embodiment, well 20 is a circular cylindrical tube which has an outer threaded surface 22 to facilitate its coupling to both reservoir 30 and cap 10. The compliant base 21, in the form of a sheet, may be draped over the lower surface of the well and clamped in place by an elastomeric e.g., Viton(TM)) O-ring or the like which fits into a groove 23 machined around the lower portion of the outer wall of the well. Use of an O-ring to couple the compliant base 21 to the well 20 is advantageous in that it allows for reusability, but other methods of attachment could also be employed. The upper surface of the well may be machined with grooves 24 into which a tool may be fit to facilitate screwing well 20 to reservoir 30.

Reservoir 30 in the embodiment shown in the figure is fabricated as a cylindrical cup with a threaded inside wall 31 to allow its coupling to well 20 by engagement with threaded surface 22. It should be appreciated that, although the illustrated embodiment shows threading means for coupling the well 20 to the reservoir 30 and cap 10, any other suitable coupling means, by which airtight coupling of the components to one another can be achieved, may be used. A circular hole is machined out of the bottom of the cup in such a way that a flange 34 is formed on the inside circumference of the cup into which a removable glass 33 or the like optical window is placed. A spacing ring, such as an elastomeric O-ring or, for greater reusability, a stainless steel ring, may be placed above the glass window 33 to form a gas and fluid-tight seal and to allow for a spacing below compliant base 21 when the well 20 and reservoir 30 are coupled. A port 32 is supplied through the wall, through the O-ring, and into the gap below the compliant base 21 and above the optical window 33 so that a regulated positive displacement pump or pressure/vacuum source may be connected to the reservoir.

A fluid or gas pressurizing medium, preferably humidified air, is injected or withdrawn from the reservoir, an associated hydrostatic pressure develops beneath the compliant base 21 causing the base to deform into a spherical cap which imparts a substantially uniform biaxial strain to all of the attached cells. Likewise, as the pressurizing medium is withdrawn, a vacuum is created below the base causing the base with the attached cells to deform in the opposite direction.

The use of a gas rather than a fluid as the pressurizing medium is preferred in several instances. First, sequential inflation and deflation of the compliant base is more readily accomplished using a gas as gas is capable of being more easily and rapidly injected and withdrawn from the reservoir. Second, the size of the reservoir and the overall device is not as restricted when gas is used as the pressurizing medium. When a larger sized apparatus is desired, or when it is desired to connect several devices at once via a manifold, the amount of fluid needed to fill the reservoir(s) and properly inflate the membrane becomes unmanageable. On the other hand, a tank of gas can conveniently provide sufficient medium to pressurize a reservoir of any size or a series of reservoirs. Finally, the use of a gas pressurizing medium is often preferred because damaging leaks are less likely.

By providing conventional control features and timing circuitry for the input or withdrawal of the gas or fluid, the magnitude and temporal nature of the mechanical stimulation of the cells can be controlled. For example, conventional wave-shaping and control circuitry can be used to wave shape the pressure input to the reservoir in order to deform the compliant base in a manner which accurately reproduces physiological strains.

Well 20 is connected above to removable cap 10, e.g., by engagement of threading means 22 with threading means 11 on the interior surface of cap 10. Cap 10 is removable to allow for conventional physiologic and biochemical tests and so that cell culture maintenance can be performed with ease under sterile conditions. Cap 10 is fabricated in a fashion similar to that of reservoir 30 without a port in its wall. It is an inverted cup with internal threads 11, permitting its coupling to the top of well 20, with a circular hole machined in the base of the cup, forming a flange 12 into which a removable glass or the like optical window 22 is placed. A spacing ring, such as an elastomeric O-ring or stainless steel ring or the like, may be used as a spacer to hold the glass 22 in place above the well 20. When coupled to well 20, an air-tight seal is formed which allows for use of the chamber in a warm room or in a conventional incubator or the like. The embodiment of the apparatus is compatible with conventional incubators and permits preassembled gas or autoclave sterilization.

Any biologically compatible, synthetic or natural, elastomeric membrane displaying elastic properties for the range of strains desired can be used as compliant base 21. The compliant base 21 may be permeable or non-permeable, the latter type being suitable for use when a gas as is being used to create the pressure flows in the reservoir 30 and the former type being suitable for use when a fluid such as culture medium with serum is pumped into the reservoir. The membrane is preferably one which can be classified in mechanical engineering terms as a membrane and for which the equations defined below can be used to relate the applied hydrostatic pressure to the subsequent strain (L. Thibault et al., "Mechanical Characterization of Membrane-Like Biological Tissue," *J Biomech Eng.* 105:31, 1983).

When a circular membrane is clamped around its periphery and subjected to a hydrostatic pressure from below, its centerline deflection, $w_o$, can be derived from known properties and the applied pressure as predicted by the following equation:

$$w_o = (0.572)a[(P)a/Eh]^{1/3}$$

where
$w_o$ = center-line deflection
a = inner radius of the well
p = pressure
E = Young's modulus
h = thickness of the compliant base With the assumptions of uniformity, homogeneity, linear elasticity and isotropy, the strain throughout 95% of the membrane can be determined using this centerline deflection, $w_o$, and the radius of the well from the following relationship:

$$e = 0.67(w_o^2/a^2)$$

where e = biaxial strain.

In the preferred embodiment, a polyurethane urea film such as Mitrathane(TM) (Matrix Medica, Denver Colo.) is selected for use as the compliant base. This membrane is preferable for several reasons. First, it allows for large deflections with modest volumes of gas, making it practical to run experiments off low pressures for many days. In addition, this membrane exhibits elastic properties to 700% elongation, allowing for a large range of strains. It is optically transparent allowing for direct microscopic visualization of the deforming cells and it does not exhibit auto-fluorescence permitting fluorescence studies to be performed on the cells with little background.

In a typical mode of operation for use of the device of this invention to study fetal bovine pulmonary artery endothelial cells, the assembled chamber is sterilized in the autoclave after which the well is seeded at a density of 100,000 cells per cm$^2$ with cloned cell strains which have been isolated and maintained as previously described (E. Macarak et al., "Growth Properties of Calf Aortic Endothelial Cells in Culture," *Lab. Invest.* 36:62, 1977). Conventional cell culture techniques are used to seed the well with cells which attach to the compliant base, spread, and divide. At this seeding density, the cells attach and become confluent overnight. Cells seeded in the well-reservoir assembly in this manner have been subjected to biaxial strains and morphometry and biochemical studies have been performed.

Using these confluent cultures grown on the Mitrathane (TM) membrane which served as the compliant base in this example, the cells' surface area change was measured with increased static strain of the Mitrathane (TM) membrane. Light microscopic photographs of the monolayer were obtained with serial, static inflations of the compliant base of the well and area changes of characteristic cells were correlated with the strain. In addition, the endothelial cells grown in the wells were subjected to a 4.9% cyclic biaxial strain at 1 Hz, that which the artery wall experiences with each pressure pulse. Experiments were terminated after 24 and 48 hours and the average type III collagen in the media at each of these experimental time lengths was assayed by competitive ELISA's, normalizing the values for cell number. For Type III collagen, a mouse monoclonal anti-type III collagen antibody and a goat anti-mouse alkaline phosphatase conjugate (Sigma) were used. Cells grown on the Mitrathane (TM) membrane and exposed to agitation with no inflation and no agitation/no inflation were used as controls. After 24 hours, the average type III collagen level harvested from the media bathing the strained cells was 9.21 ng/cell with the control value at 6.96 ng/cell. While at 48 hours, the average type III Collagen per cell was 40.7 ng/cell in the strained cells versus 29.65 ng/cell in the unstrained cells. Even at these low levels of strain, short experimental time lengths, and relatively slow frequencies, over a 30% increase in collagen production was seen which would result in greater harvesting efficiency of collagen from endothelial cells in culture.

In another study utilizing bovine pulmonary artery endothelial cells, the cells were grown on polyurethane urea film in the device of this invention and were subjected to cyclic biaxial strain for 7-48 hours. Strains ranging from 0.78% to 12.5% at a frequency of 1 Hz were employed. Fibronectin (Fn)in the medium of these cells was measured by competitive ELISA. At strains of 4.9% or greater applied for seven hours, the concentration of Fn per cell was reduced when compared to either non-stressed stationary or agitated controls. The percent reduction ranged from 23% to 56% but was not directly proportional to the degree of strain. After 24 or 48 hours of 4.9% cyclic biaxial strain, the fibronectin levels in the medium of stressed cells return to control values; however, there is an increased amount of type III collagen in the medium of stressed cells. Preliminary data from 24 hour radio-labelling experiments indicate that there is no qualitative difference in the proteins secreted by stressed vs. non-stressed cells, although there appears to be more protein (in particular, type III collagen) incorporated into the extracellular matrix of stressed cells.

While a specific embodiment of an improved method for culturing cells under their in vivo mechanical environment has been disclosed in the foregoing description, it will be understood that various modifications within the scope of the invention may occur to those skilled in the art. Therefore, it is intended that adaptations and modifications should and are intended to be comprehended within the meaning and range of equivalents of the disclosed embodiment. For example, use of the proposed invention with endothelial cells was described, but other cell types are equally adaptable.

What is claimed is:

1. A method for studying cells in culture under conditions which reproduce their natural, in vivo mechanical environment comprising
   providing a device comprising
      an airtight well having an optically transparent circular compliant base of a biologically compatible material on which said cells may be grown and an optically transparent, removable cap, which airtight well and removable cap are formed of biologically compatible materials, and
      a ported, airtight reservoir coupled with said well beneath said compliant base, which reservoir has an optically transparent base;
   seeding said cells on said compliant base;
   allowing said cells to become confluent and attach to said compliant base;
   injecting into and withdrawing from said airtight reservoir gaseous medium to create cyclic variations in hydrostatic pressure beneath said compliant base to concavedly-convexedly deform and thereby exert a substantially uniform biaxial strain on the cells attached thereto.

2. The method of claim 1 wherein said compliant base is a polyetherurethane urea film.

3. The method of claim 1 wherein said well, cap and reservoir are partially fabricated of stainless steel.

4. The method of claim 1 in which said compliant base is selected so that the biaxial strain exerted on said cells may be predicted from the hydrostatic pressure applied from below by the following equation:

$$\text{biaxial strain} = 0.67(w_o^2/a^2)$$

where
   a = inner radius of the well
   $w_o = (0.572)a[(P)a/Eh]^{1/3}$
where
   p = pressure applied from below
   E = Young's modulus
   h = thickness of compliant base.

5. The method of claim 4 in which said compliant base exhibits substantially no auto-fluorescence.

6. The method of claim 4 in which said compliant base is a polyetherurethane urea film.

7. The method of claim 1 in which the gaseous medium is humidified air.

8. The method of claim 1 wherein said cells are endothelial cells.

9. The method of claim 8 wherein said cells are subjected to a cyclic biaxial strain of about 4.9% at 1 Hz.

10. The method of claim 1 in which said variations in hydrostatic pressure are wave shaped.

* * * * *